United States Patent
Mukai

(10) Patent No.: US 6,641,578 B2
(45) Date of Patent: Nov. 4, 2003

(54) LASER TREATMENT APPARATUS

(75) Inventor: Hideo Mukai, Toyohashi (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 09/887,018

(22) Filed: Jun. 25, 2001

(65) Prior Publication Data

US 2002/0049432 A1 Apr. 25, 2002

(30) Foreign Application Priority Data

Jun. 28, 2000 (JP) .................................... 2000-200060

(51) Int. Cl.$^7$ ................................................ A61B 18/18
(52) U.S. Cl. ......................... 606/9; 606/10; 606/11; 606/12; 607/88
(58) Field of Search .................... 606/8–13, 16, 606/127; 128/898

(56) References Cited

U.S. PATENT DOCUMENTS

| | | | |
|---|---|---|---|
| 4,813,412 A | * 3/1989 | Yamazaki et al. | 128/303.13 |
| 5,016,173 A | 5/1991 | Kenet et al. | |
| 5,501,680 A | * 3/1996 | Kurtz et al. | 606/9 |
| 5,630,811 A | 5/1997 | Miller | |
| 6,074,382 A | 6/2000 | Asah et al. | |
| 6,162,211 A | * 12/2000 | Tankovich et al. | 606/9 |
| 6,162,212 A | * 12/2000 | Kreindel et al. | 606/9 |
| 6,165,170 A | * 12/2000 | Wynne et al. | 606/9 |
| 6,273,883 B1 | * 8/2001 | Furumoto | 606/9 |
| 6,436,127 B1 | * 8/2002 | Anderson et al. | 607/89 |
| 6,447,503 B1 | * 9/2002 | Wynne et al. | 606/9 |

FOREIGN PATENT DOCUMENTS

| | | | |
|---|---|---|---|
| EP | 0 880 941 A1 | 12/1998 | |
| EP | 1 031 324 A1 | 8/2000 | |
| EP | 1 057 454 A2 | 12/2000 | |
| JP | A 5-146517 | 6/1993 | |
| JP | A 2000-501016 | 2/2000 | |
| JP | 245525 | * 12/2000 | .......... A61B/18/20 |

* cited by examiner

*Primary Examiner*—Linda C. M. Dvorak
*Assistant Examiner*—Ahmed Farah
(74) *Attorney, Agent, or Firm*—Oliff & Berridge, PLC

(57) ABSTRACT

A laser treatment apparatus for performing treatment by irradiating a skin of a patient with a laser beam for treatment is disclosed. The apparatus includes: an irradiation unit including a laser source which emits a treatment laser beam and an irradiation optical system which delivers the treatment laser beam from the laser source to a treatment part of the skin to irradiate the part; a skin color detection unit including an imaging element which takes a picture image of the skin to be irradiated and an image processing section which detects a color of the imaged skin; a determination unit which determines an irradiation condition including at least one of output power of the treatment laser beam, irradiation time, irradiation density, and irradiation energy; a memory which stores data on the skin color detected by the detection unit and, in association therewith, data on the irradiation condition determined by the determination unit; and a control section which automatically determines an irradiation condition based on data on a skin color that is newly detected and the data having been stored in the memory, and transmits a control signal representative of the determined irradiation condition to the irradiation unit for control of irradiation of the treatment laser beam.

6 Claims, 5 Drawing Sheets

FIG. 6

| SKIN COLOR | DARK ← → LIGHT | | | | | | | | | |
|---|---|---|---|---|---|---|---|---|---|---|
| HAIR THICKNESS | A | B | C | D | E | F | G | H | I | J |
| THIN ↑ 1 | A1 | B1 | C1 | D1 | E1 | F1 | G1 | H1 | I1 | J1 |
| 2 | A2 | B2 | C2 | D2 | E2 | F2 | G2 | H2 | I2 | J2 |
| 3 | A3 | B3 | C3 | D3 | E3 | F3 | G3 | H3 | I3 | J3 |
| 4 | | | | | ⋮ | | | | | |
| 5 | | | | | ⋮ | | | | | |
| 6 | | | | | ⋮ | | | | | |
| 7 | | | | | ⋮ | | | | | |
| 8 | | | | | ⋮ | | | | | |
| ↓ THICK 9 | | | | | | | | | | |
| 10 | A10 | B10 | C10 | D10 | E10 | F10 | G10 | H10 | I10 | J10 |

# LASER TREATMENT APPARATUS

BACKGROUND OF THE INVENTION

1. Field of the Invention

The present invention relates to a laser treatment apparatus for performing treatment by irradiating a skin of a patient with a laser beam for treatment.

2. Description of Related Art

There has been known a laser treatment apparatus for irradiating a skin of a patient with a laser beam for treatment (hereinafter referred to as a treatment beam) to remove birthmarks, stains, tattoos being on the skin or to cause depilation. A type of this apparatus needs that irradiation conditions such as output power, irradiation time, irradiation density, and irradiation energy of the treatment beam are appropriately determined in consideration of a state of a treatment part of the patient's skin. In laser treatment for depilation, for instance, an optimum value of the output power of the treatment beam with respect to the skin of a patient to be treated is determined by a test-irradiation of the treatment beam to the skin. In this test-irradiation, the intensity of the treatment beam is gradually increased until the patient feels a pain on the skin, and then the power is set to a value slightly lower than the value at which the patient feels a pain. In the laser depilation treatment, furthermore, an operator observes the thickness of a hair in advance and sets the irradiation condition based on his own experience.

However, the state of the skin and the treatment part is different from patient to patient. Determining the optimum irradiation condition with the treatment beam test-irradiated would give troublesomeness to the operator and impose a large burden on the patient. Setting the irradiation conditions in consideration of the thickness of a hair for the laser depilation treatment largely depends on the operator's experience. When the output power of the treatment beam is too strong or the irradiation time thereof is too long, the possibility that the treatment beam damages the skin would increase. When the output power is too low or the irradiation time is too short, to the contrary, the treatment (depilation) could not surely, efficiently be achieved.

SUMMARY OF THE INVENTION

The present invention has been made in view of the above circumstances and has an object to overcome the above problems and to provide a laser treatment apparatus capable of easily determining optimum irradiation conditions according to the color of a skin (and further the thickness of a hair for depilation) to perform efficient treatment (depilation) with less damage to the skin.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for performing treatment by irradiating a skin of a patient with a laser beam for treatment, the apparatus including: an irradiation unit including a laser source which emits a treatment laser beam and an irradiation optical system which delivers the treatment laser beam from the laser source to a treatment part of the skin to irradiate the part; a skin color detection unit including an imaging element which takes a picture image of the skin to be irradiated and an image processing section which detects a color of the imaged skin; a determination unit which determines an irradiation condition including at least one of output power of the treatment laser beam, irradiation time, irradiation density, and irradiation energy; a memory which stores data on the skin color detected by the detection unit and, in association therewith, data on the irradiation condition determined by the determination unit; and a control section which automatically determines an irradiation condition based on data on a skin color that is newly detected and the data having been stored in the memory, and transmits a control signal representative of the determined irradiation condition to the irradiation unit for control of irradiation of the treatment laser beam.

According to another aspect of the present invention, there is provided a laser treatment apparatus for performing treatment by irradiating a skin of a patient with a laser beam for treatment, the apparatus including: an irradiation unit including a laser source which emits the treatment laser beam and an irradiation optical system which delivers the treatment laser beam from the laser source to a treatment part of the skin to irradiate the part; a skin color detection unit including an imaging element which takes a picture image of the skin to be irradiated and an image processing section which detects a color of the imaged skin; a memory which stores, in a table form, data on a plurality of skin colors classified into plural kinds by a predetermined reference and data on irradiation conditions associated with the kinds of skin colors individually, the irradiation conditions including at least one of output power of the treatment laser beam, irradiation time, irradiation density, and irradiation energy; and a control section which automatically determines an irradiation condition based on data on a skin color that is newly detected by the detection unit and the table having been stored in the memory, and transmits a control signal representative of the determined irradiation condition to the irradiation unit for control of irradiation of the treatment laser beam.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 6 is a table providing the darkness of a skin color and the thickness of a hair, used for determining an optimum irradiation condition.

DETAILED DESCRIPTION OF THE PREFERRED EMBODIMENTS

Figure 1:
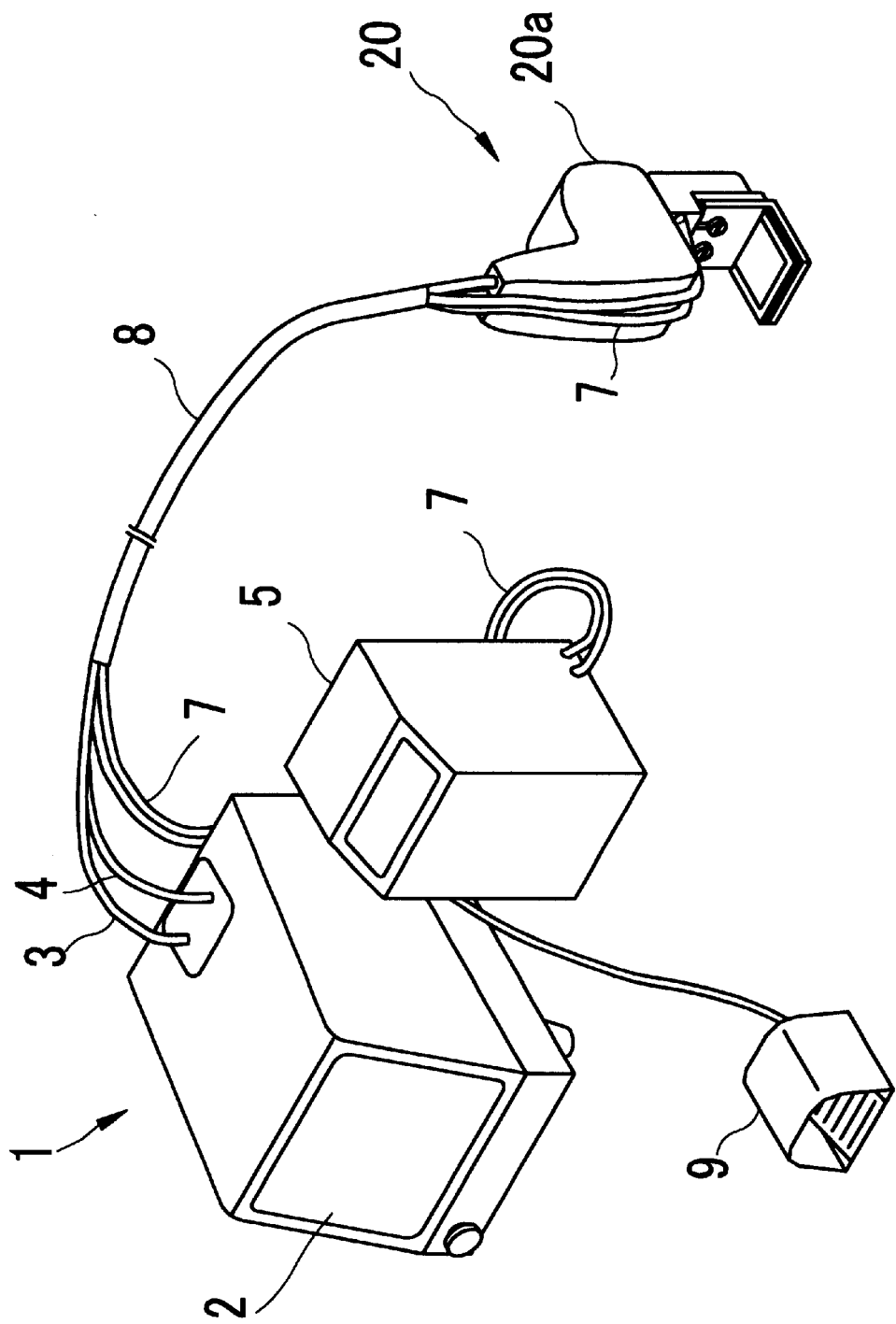
FIG. 1 is a schematic perspective view of a laser treatment apparatus in an embodiment according to the present invention.
Figure 2:
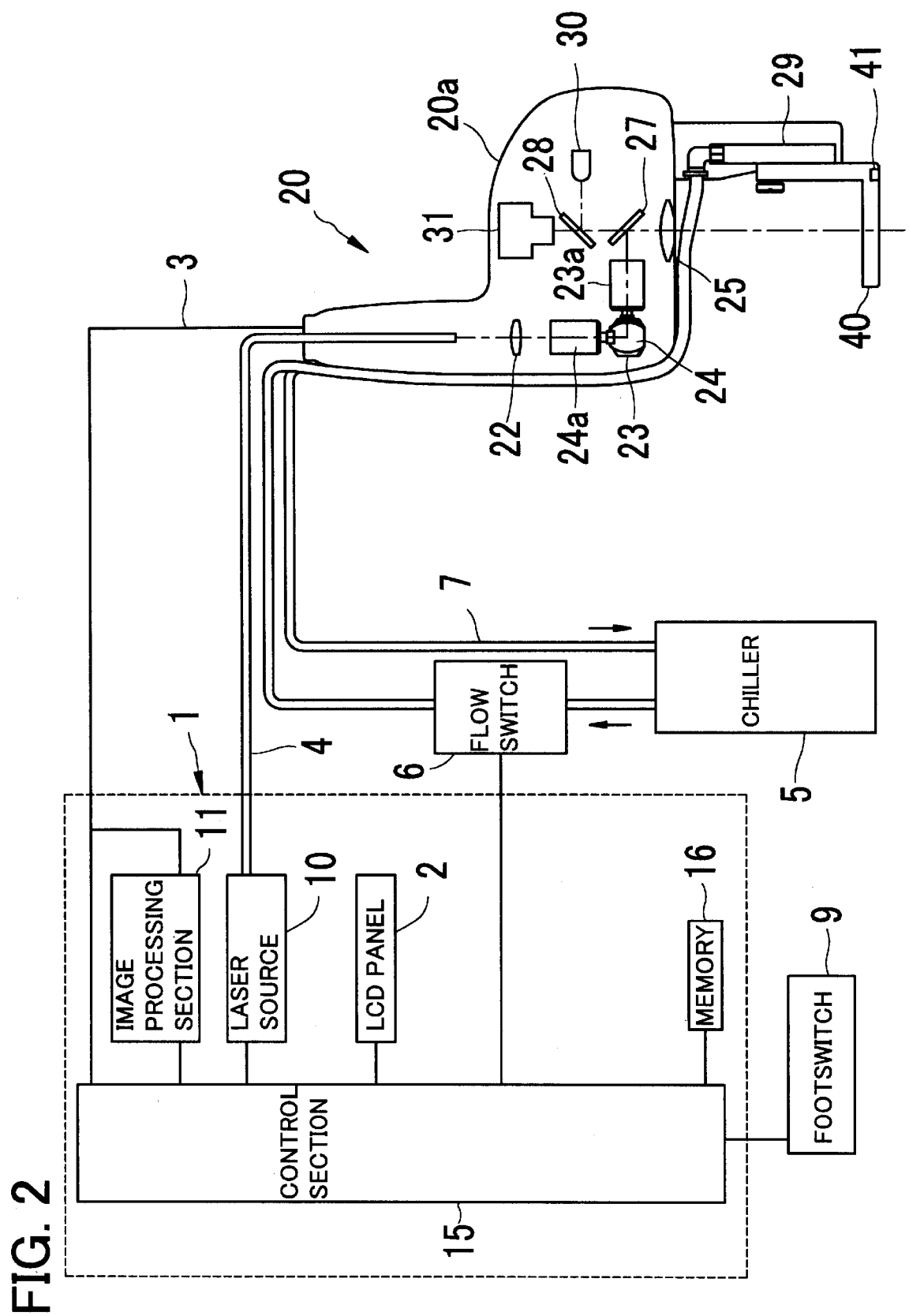
FIG. 2 is a schematic view of an optical system and a control system in the apparatus in the embodiment.

A detailed description of a preferred embodiment of a laser treatment apparatus embodying the present invention will now be given referring to the accompanying drawings. FIG. 1 is a schematic perspective view of a laser treatment apparatus to be used for treatment such as depilation. FIG. 2 is a schematic view of an optical system and a control system in the apparatus in the present embodiment.

Figure 3:
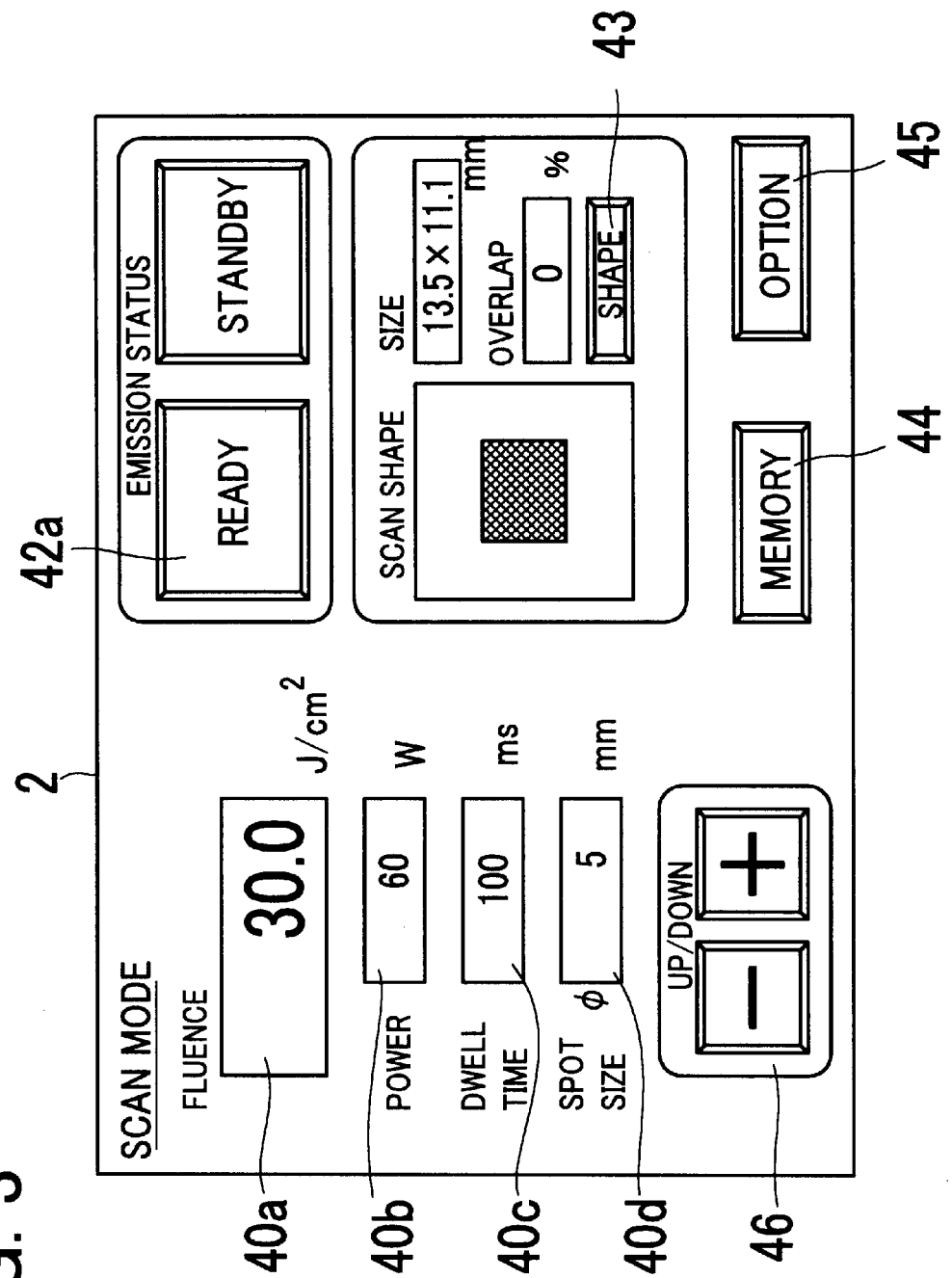
FIG. 3 is a layout view of operation keys (buttons) on an LCD panel.

A main unit 1 of the apparatus is provided with a large-sized liquid crystal display (LCD) panel 2 on the front side. This LCD panel 2 is a touch panel on which various determined irradiation conditions and plural operation keys or buttons are displayed as shown in FIG. 3. Those keys or buttons on a display screen of the LCD panel 2 are selectively touched to alter the irradiation conditions (which will be mentioned later in detail).

A signal cable 3 and a fiber cable 4 are provided extending from the top of the main unit 1 to a handpiece 20 which projects the treatment beam.

Numeral 5 is a chiller for cooling a coolant circulating therein to supply the cooled coolant to the handpiece 20. Two tubes 7 extending from the chiller 5 are bundled with the cable 3 and the fiber 4 into one concentration cable 8. Numeral 9 is a footswitch for issuing a trigger signal to start laser irradiation (irradiation of the treatment beam) when pressed.

In FIG. 2, numeral 10 is a laser source section including a laser diode which emits a laser beam for treatment (a near infrared laser beam of wavelengths of 800 to 820 nm) and another laser diode which emits a visible laser beam for aiming (a red visible laser beam of wavelengths of 620 to 650 nm). The laser beams; the treatment beam and the aiming beam emitted from the laser source section 10 become incident on the fiber 4. This fiber 4 is connected to the handpiece 20, delivering the laser beams to the handpiece 20.

In a scanner head 20a of the handpiece 20, there are provided a first mirror 23 and a second mirror 24. When these mirrors 23 and 24 are rotated (swung) by means of a first galvanometer 23a and a second galvanometer 24a respectively, an irradiation site (position) of the treatment beam (and the aiming beam) is shifted in X- and Y-directions, thus scanning a wide region. The treatment beam (and the aiming beam) having entered the scanner head 20a through the fiber 4 is collimated by a collimator lens 22 and deflected by the swinging mirrors 23 and 24 in the X- and Y-directions. Thereafter, the beam is reflected by a dichroic mirror 27 toward the treatment part and then focused (concentrated) by a focusing lens 25 into a circular spot of about 5 mm in diameter on the treatment part (near the underside of the window 40). The dichroic mirror 27 has properties of reflecting the treatment beam and a part of the aiming beam, while transmitting a large part of visible light.

In the inside of the scanner head 20a, an observation camera 31 is disposed to take a picture image of the treatment part. The light from the illumination light source 30 is reflected by a half mirror 28, allowed to pass through the dichroic mirror 27 and the lens 25, illuminating the treatment part. The quantity of light from the light source 30 is determined larger than that of extraneous light to thereby prevent the skin color from being influenced by the extraneous light. The reflection light from the treatment part is allowed to pass through the lens 25, the dichroic mirror 27, and the half mirror 28, and becomes incident on the camera 31. A signal from the camera 31 is then transmitted to the main unit 1 where an image processing section 11 analyzes the skin color of the treatment part and the thickness of the hair therein.

The scanner head 20a is provided, in the lower portion, with a window 40 including a glass board which transmits the laser beams and visible light. This window 40 is pressed against the skin to flatten the surface of the treatment part and cool it as below.

A cooling plate 29 is fixed to the window 40. This plate 29 is internally provided with a passage for circulating coolant. The coolant cooled in the chiller 5 is delivered through the tube 7 to the cooling plate 29 and circulated therein, which absorbs the heat of the window 40 through the cooling plate 29, absorbing in turn the heat of the skin. Through this series of heat transfer, the window 40 cools the treatment part. The window 40 is also provided with a touch sensor 41 on the underside.

A control section 15 in the main unit 1 is connected to the LCD panel 2, a flow switch 6, a memory 16, a footswitch 9, and others. The flow switch 6 is used to check whether the coolant normally circulates from the chiller 5 to the cooling plate 29. The first and second galvanometers 23a and 24a, the light source 30, the camera 31, the touch sensor 41 are connected to the control section 15 through the cable 3.

Operations of the laser treatment apparatus constructed as above will be described below.

Figure 4:
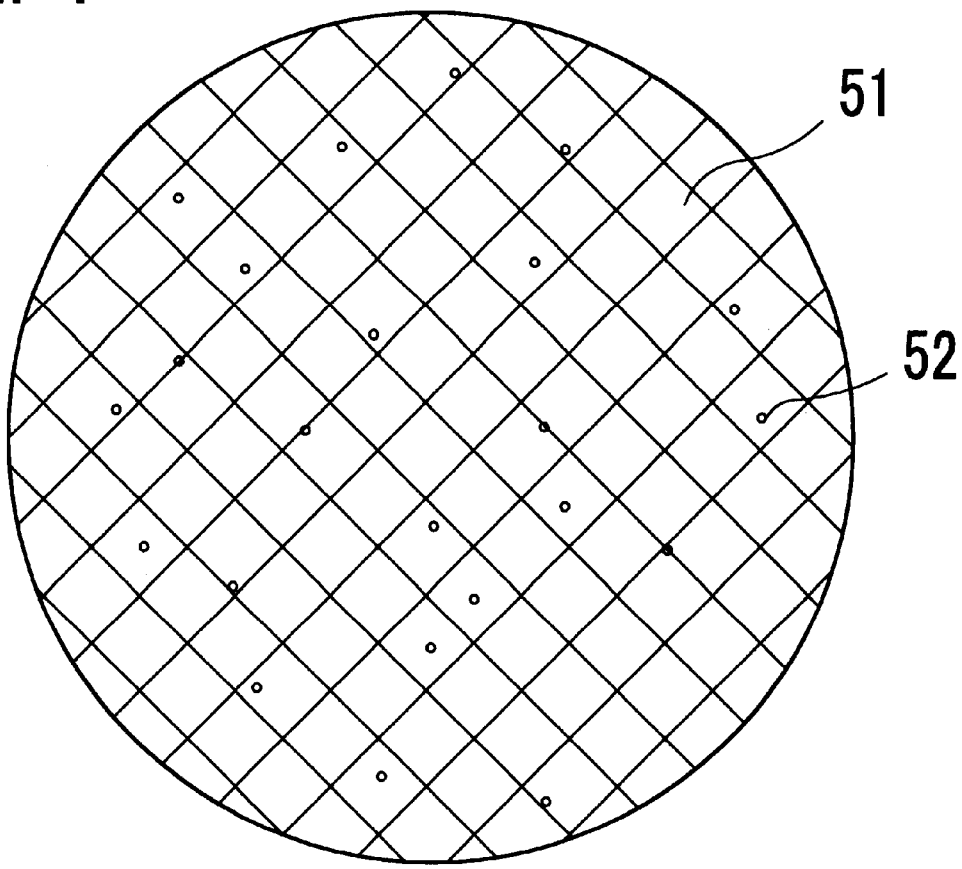
FIG. 4 is a schematic view showing an image of a treatment part for observation.

The operator holds the handpiece 20 by hand and brings the window 40 in contact with on the treatment part (skin) of the patient. When the touch sensor 41 detects that the window 40 is in contact with the treatment part, the light source 30 is turned on and the camera 31 takes a picture image of the treatment part illuminated by the light from the light source 30. The image signal from the camera 31 is input in the image processing section 11, which averages and detects the darkness (light and dark) 51 of the skin color as shown in FIG. 4.

The handpiece 20 projects the aiming beam. This aiming beam is repeatedly scanned by operation of the first and second mirrors 23 and 24 in accordance with the shape of a scanning pattern previously selected with a key (button) 43. The operator observes the aiming beam which is being projected on the skin through the window 40, and makes alignment of the aiming beam to the treatment part. The treatment beam is irradiated as follows: a key (button) 42a on the LCD panel 2 is pressed, which brings the apparatus into a READY state where the treatment beam can be irradiated; and the footswitch 9 is then pressed, entering a trigger signal to start the laser irradiation. Upon receipt of the trigger signal, the control section 15 causes the laser source section 10 to emit the treatment beam. The treatment beam is scanned as with the aiming beam to irradiate the treatment part.

Prior to the above laser irradiation, it is necessary for the operator to set appropriate irradiation conditions with keys (buttons) on the LCD panel 2 (see FIG. 3) in consideration of the skin color and the hair condition. On the LCD panel 2 there are provided a display part 40a for energy density, a display part 40b for output power, a display part 40c for pulse irradiation time, and a display part 40d for spot size. Each set value indicated on the display parts can be changed with push of the target display part and then an UP/DOWN key (button) 46. A spot diameter of the laser beam can be changed by replacement of the lens 25 with an appropriate one for a desired spot diameter. In adjusting the irradiation conditions, for example, the output power (or the pulse irradiation time) is initially adjusted to the low side. Sequentially, the treatment beam is test-irradiated to the patient's skin, while the output power is raised to gradually increase the laser energy up to the level at which the patient will not complain of a skin pain.

The relation between the skin colors and the irradiation conditions is explained below. The laser depilation is executed thus: a treatment beam is absorbed into melanin present around hair roots; and accumulated heat energy is propagated to the hair roots and thus cauterizes the hair roots. In this laser depilation, energy whose amount is so moderate as not to destroy melanin of the skin but large enough to cauterize hair roots must be provided. In general, the amount of melanin is proportional to the darkness of the skin color; a darker skin contains a larger amount of melanin therein and around hair roots than a fairer skin.

Accordingly, the energy of the treatment beam to be irradiated to the darker skin is adjusted lower, while the beam energy to the fairer skin is set higher.

After completion of final setting of the irradiation conditions at desired values, the operator pressed a key (button) 44. When this key 44 is pressed, the memory 16 stores the data on the irradiation condition currently set in correspondence with the data on the skin color of the patient detected as above in the image processing section 11.

The irradiation condition data adjusted by the operator as above and the skin color data are stored in the memory 16 every time treatment is conducted in the form of a table presenting their correspondence. In the next treatment, an irradiation condition is automatically set based on the stored data. To be more specific, when the handpiece 2 is put on the skin in contact therewith at the initial step of treatment, the color of the skin is detected from the picture image taken by the camera 31 in the above-mentioned manner. The control section 15 calls the irradiation condition associated with the detected color from the table providing skin colors and irradiation conditions, automatically setting it as an initial condition (initial values). This could reduce troublesomeness for an operator in setting the irradiation condition. Even if the automatically set condition needs to be adjusted, its adjusting variation is little, which facilitates selection of an optimum condition for the patient's skin. When the irradiation condition is adjusted, the key 44 is pressed, causing the memory 16 to store the irradiation condition as the latest information corresponding to the detected skin color.

In the above manner, the control section 15 automatically determines the irradiation condition based on the result of detection of the skin color. If there is no data on an irradiation condition corresponding to the newly detected skin color, an irradiation condition associated with the most similar color among the color data stored in the memory 16 is selected. In this case, an irradiation condition including a lower energy value may be selected from among several conditions associated with the similar colors. Alternatively, the irradiation condition to be determined may be calculated according to a ratio of color similarity.

Figure 5:
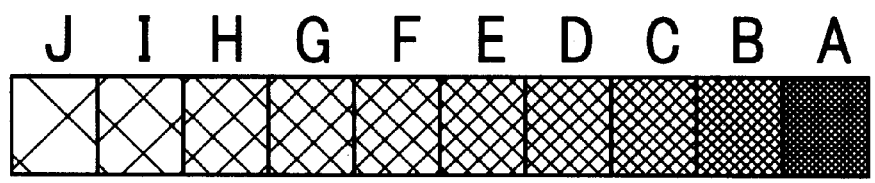
FIG. 5 is a classified scale of the darkness of a skin color divided into ten ranks, A to J.

The table providing the skin color data and the irradiation condition data may be produced by ranking the detected color to be stored in the memory 16 by darkness. As shown in FIG. 5, for example, skin colors are classified in advance into ten ranks, A to J. If data on plural irradiation conditions are stored in association with the same rank, the data on an irradiation condition including an average or middle value or the lowest energy value is automatically determined as the initial condition.

Such the table with color ranking may be produced in advance based on standard irradiation conditions and stored in the memory 16 so that an irradiation condition is automatically in accordance with the table at the time of treatment. In this case, when the operator changes the data on the irradiation condition associated with the color rank F in FIG. 5, the changed data is stored in the table in the memory 16 at the push of the key 44.

At the time of treatment with respect to a different color rank (A to E, G to J), the values of the table are made offset by an amount equal to the changed amount of data adjusted for the color rank F, and the irradiation condition with the offset values is automatically determined as an initial condition. The changed amount is averaged every time the data is accumulated.

Furthermore, it may be arranged that the previously stored table is rewritten every time the operator presses the key 44 to store the irradiation condition after adjustment. In this case, a key 45 on the LCD panel 2 is pressed to open a setting change screen, where a table rewriting mode can be selected.

As explained above, the condition adjusted by the operator is sequentially stored in every treatment on plural patients. In the apparatus, therefore, the way of determining conditions comes close to the concept of the operator. In other words, the data determined empirically by the operator is accumulated in the apparatus, which enables instantaneous selection of an optimum irradiation condition even for a first-time patient. If the irradiation condition has to be adjusted, on the other hand, it does not need to be largely changed, which would reduce troublesomeness for the operator.

In the above description, the automatic determination of an irradiation condition is based on the detected skin color. The following explanation is made on the determination based on the thickness of a hair in addition to the skin color. The image processing section 11 first judges from the picture image taken by the camera 31 (FIG. 4) that portions 52 are hairs in consideration of their color and shape. The cross-sectional area of each of the hairs is calculated, and the calculated values are averaged to determine a hair thickness. The hair thickness thus determined by average is numerically classified into ten ranks (1 to 10). However, there may be cases where thin hairs have been cut or shaved, so that the hair thickness could not clearly be determined only from the image taken by the camera. In this case, the following manner is adopted.

This manner is described for example in EP-A1-1031324 (corresponding to Japanese patent unexamined publication No. 2000-245525) filed by the same applicant as the present invention. A treatment beam of lower output power is diffusely irradiated, which is used for detection. The distribution of temperatures in the irradiated region is recorded by a thermograph. Points indicating high temperatures are distinguished based on the record, whereby the positions of hair roots can be specified.

The thickness of each hair root can be detected by measuring the area of the center of each of the points indicating the high temperatures. In this case, similarly, the thickness values are averaged and numerically classified into ten ranks (1 to 10).

As with the former case, the operator presses the key 44 to store the irradiation condition after adjustment in the memory 16 in every treatment. Thus, a table is produced to provide the irradiation conditions which are associated with both the darkness of a skin color and the thickness of a hair as parameters, as shown in FIG. 6. At the start of treatment, an irradiation condition is automatically determined from the table in correspondence with the detection result about the skin color and the hair thickness. When no data corresponding to the detected skin color and hair thickness is in the table, an irradiation condition is determined with reference to other data on the most similar color and thickness in the table as with the above-mentioned case.

According to the present invention, as explained above, an optimum irradiation condition can readily be determined according to the color of a patient's skin, which enables efficient treatment with less damage to the skin. Furthermore, in the laser depilation, an irradiation condition can easily be determined in consideration of the thickness of a hair in addition to the skin color.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated.

It is intended that the scope of the invention be defined by the claims appended hereto, and their equivalents.

What is claimed is:

1. A laser treatment apparatus for performing treatment by irradiating a skin of a patient with a laser beam for treatment, the apparatus including:

an irradiation unit including a laser source which emits the treatment laser beam and an irradiation optical system which delivers the treatment laser beam from the laser source to a treatment part of the skin to irradiate the part;

a skin color detection unit including an imaging element which takes a picture image of the treatment part of the skin to be irradiated and an image processing section which detects a color of the imaged part of the skin;

a memory which stores data on a plurality of different darknesses of skin color and data on a plurality of different values of irradiation condition associated individually with each other, the irradiation condition including at least one of output power of the treatment laser beam, irradiation time, irradiation density and irradiation energy, the irradiation condition value being lower as the skin color darkness becomes darker; and a control section which automatically determines a value of the irradiation condition corresponding to the darkness of the skin color that is newly detected based on the data stored in the memory so that, when no data on darkness substantially the same as the newly detected darkness is in the stored data, the irradiation condition value corresponding to the most similar darkness which is darker than the newly detected darkness is determined.

2. The laser treatment apparatus according to claim 1, further including a hair thickness detection unit which detects a thickness of a hair within the treatment part, wherein the memory stores data on a plurality of different hair thicknesses and the data on the irradiation condition values associated individually with each other, the irradiation condition value being lower as the hair thickness becomes thinner, and the control section automatically determines a value of the irradiation condition corresponding to hair thickness that is newly detected based on the data stored in the memory so that, when no data on a thickness substantially the same as the newly detected thickness is in the stored data, the irradiation condition value corresponding to the most similar thickness which is thinner than the newly detected thickness is determined.

3. The laser treatment apparatus according to claim 1, wherein the irradiation unit includes a handpiece provided with a part of the irradiation optical system, and the imaging element is provided in the handpiece.

4. The laser treatment apparatus according to claim 1, wherein the irradiation optical system includes an optical member which shapes the treatment laser beam into a small spot on the treatment part and a scanning optical system which scans the treatment laser beam within a predetermined first area, and the imaging element takes an image of a predetermined second area including the first area.

5. A laser treatment apparatus for performing treatment by irradiating a skin of a patient with a laser beam for treatment, the apparatus including:

an irradiation unit including a laser source which emits the treatment laser beam and an irradiation optical system which delivers the treatment laser beam from the laser source to a treatment part of the skin to irradiate the part;

a skin color detection unit including an imaging element which takes a picture image of the treatment part of the skin to be irradiated and an image processing section which detects a color of the imaged part of the skin;

a memory which stores, in a table form, data on a plurality of different darknesses of skin color and data on a plurality of different values of irradiation condition associated on a one to one basis with each other, the irradiation condition including at least one of output power of the treatment laser beam, irradiation time, irradiation density, and irradiation energy;

a control section which automatically determines a value of the irradiation condition corresponding to the darkness of the skin color that is newly detected based on the table stored in the memory; and an adjustment unit by which an operator adjusts the irradiation condition value, wherein the control section automatically adjusts the table based on the adjustment by the adjustment unit.

6. The laser treatment apparatus according to claim 1, further including a hair thickness detection unit which detects a thickness of a hair within the treatment part, wherein the memory stores, in a table form, data on a plurality of different hair thicknesses and the data on irradiation condition values associated on a one to one basis with each other, and the control section automatically determines a value of the irradiation condition corresponding to the hair thickness that is newly detected based on the table stored in the memory and automatically adjusts the table based on the adjustment by the adjustment unit.

* * * * *